United States Patent [19]
Neumann et al.

[11] Patent Number: 5,437,683
[45] Date of Patent: Aug. 1, 1995

[54] SURGICAL CLOSURE

[76] Inventors: Martin Neumann, Ruhsteinweg 26, D-8525 Weiher; Ferdinand Köckerling, Hindenburgstrasse 28a, D-8520 Erlangen, both of Germany

[21] Appl. No.: 50,048
[22] PCT Filed: Oct. 31, 1991
[86] PCT No.: PCT/DE91/00849
§ 371 Date: Apr. 28, 1993
§ 102(e) Date: Apr. 28, 1993
[87] PCT Pub. No.: WO92/07519
PCT Pub. Date: May 14, 1992

[30] Foreign Application Priority Data
Oct. 31, 1990 [DE] Germany ............ 40 34 705.2

[51] Int. Cl.6 ................................. A61B 17/00
[52] U.S. Cl. ......................... 606/151; 606/213; 602/41; 604/305; 604/307
[58] Field of Search ........... 606/151, 220, 213, 215, 606/216, 217; 602/41, 42; 604/305, 307, 332, 337, 338, 341, 355

[56] References Cited

U.S. PATENT DOCUMENTS

| | | | |
|---|---|---|---|
| 2,025,492 | 12/1935 | Aird | 604/355 |
| 2,524,750 | 10/1950 | Bellinger | 604/355 |
| 2,692,597 | 10/1954 | Carstensen | 604/338 |
| 3,954,105 | 5/1976 | Nordby | 604/355 |
| 4,334,530 | 6/1982 | Hassell | 602/42 |
| 4,548,202 | 10/1985 | Duncan | 606/220 |
| 4,561,858 | 12/1985 | Allen, Jr. et al. | 604/338 |
| 4,857,064 | 8/1989 | Mendoza | 604/355 |
| 4,969,880 | 11/1990 | Zamierowski | 604/305 |
| 5,086,763 | 2/1992 | Hathman | 602/42 |
| 5,263,922 | 11/1993 | Sova et al. | 604/305 |

FOREIGN PATENT DOCUMENTS

0605291 9/1960 Canada .................. 604/338

Primary Examiner—Stephen C. Pellegrino
Assistant Examiner—Jeffrey A. Schmidt
Attorney, Agent, or Firm—Sixbey, Friedman, Leedom & Ferguson; David S. Safran

[57] ABSTRACT

A surgical closure which can be repeatedly opened and closed, especially one for an abdominal incision, consisting of flexible fabric or plate-like securing means which can be firmly secured to the bodily tissue close to the incision but can be released therefrom and with a closure bringing together its end regions above the incision which can be opened and closed at any time, is to be improved in such a way that a completely pressure-tight closure is obtained but which may be opened as often as desired. This is achieved in that it is fitted with a securing component (15) surrounding the incision on all sides which has an opening (4) that can be placed above the incision and consists of a tube (5) of flexible material extending upward from and surrounding the opening (4) and the tube (5) itself acts as the closure or is fitted with such.

27 Claims, 5 Drawing Sheets

SURGICAL CLOSURE

BACKGROUND OF THE INVENTION

This invention relates to a surgical closure that can be repeatedly opened and closed, especially for the abdominal wall. More particularly the invention relates to a surgical closure having fabric of plate-like securing elements that can be tightly but detachably connected to the body tissue and has a closure which can be repeatedly opened and closed.

Such a surgical closure is known, for example, from German Patent 34 44 782. This surgical closure is used especially as a temporary closure for the abdominal cavity, preferably for postoperative treatment of peritonitis.

Peritonitis, as a secondary form that develops as a result of a perforation of a hollow organ or as a postoperative complication, still has, even today, a high lethality. With increasing incidence, it represents a central surgical problem.

The abdominal cavity is subject to a physiological, regulated fluid stream that drains mainly by small openings in the peritoneal diaphragm underside. In this way, bacteria are fed by the lymph tracts to the systemic defense mechanism. The absorption capacity of the intraperitoneal fluid is increased by the mobility of the diaphragm and intraperitoneal pressure. During peritonitis, this drainage is blocked by the pathophysiological development of fibrin and bacteria and circulation is hindered by fibrin-induced adhesions. The defense system is disrupted and a rise in bacterial counts, or their toxins and fibrin, results. If the progression of peritonitis is not stopped promptly, a pathophysiological cascade gets started whose dynamics constantly grow and, after a certain point, can no longer be stopped.

To cleanse the abdominal cavity, washing with physiological saline solution is already done during the operation until the wash fluid stays clear. With this mechanical cleansing, bacterial counts, fibrin, dead tissue, toxins and also residual blood (even hemoglobin promotes the start of an infection) are to be removed as completely as possible, to provide, along with surgical removal of septic focus, an optimal condition for healing.

In the postoperative phase, in which the fate of the patient is mainly determined, it is decisive to recognize a worsening of the condition as early as possible, and optionally, to remove the cause (e.g., correction of an inadequate suture after oversewing a gastric ulcer) and, by effective lavage, if possible from the first postoperative day forward, to make sure conditions are clean (blood that reappears, fibrin and bacteria are to be rinsed away).

In postoperative lavage, the strategy of the open abdomen with periodic washing and the wash treatment with a closed abdomen are known.

This so-called open abdomen is made possible by the sliding splint closure and by the snap closure as a temporary closure for the abdominal cavity, with the advantages that repeated intra-abdominal accessibility is guaranteed and the technician, during each washing, can be convinced of the success of the removal of septic focus, and thus, can control the course of peritonitis. In doing so, postoperative, intra-abdominal adhesions can be detached and coatings of fibrin can be removed. The typical drainage complications are eliminated. (Plugging of drainage for the abdominal wall, blockage or obstruction of drainages, infection sources.) A relaparotomy is no longer necessary.

Here, the drawback is that right after the operation, washing cannot be performed and no continuous washing is possible. But then, periodic washing is relatively frequent and also a burden for the patient, when the patient is in critical condition. Periodic washing must be prepared carefully; it is performed in the operating room (the abdomen is open during washing) and under general anesthesia. The advantages of the principle of peritoneal dialysis must be done without, since previous temporary abdominal cavity closures do not close the abdomen tightly. The wash effect remains limited, since a desired intra-abdominal pressure is not maintained, and the wash fluid flows, preferably, only in preformed wash channels. Further, after the temporary closure of the abdominal wall, part of the wash fluid oozes into the bed which, in addition to being another source of infection, means ineffective washing, additional burden for the patient, and considerable additional expense for the nursing staff. Patients with an open abdomen belong, at that time, to the most care-intensive patients. If a so-called snap closure or sliding splint closure, as a temporary abdominal cavity closure, is infolded, another drawback comes to bear. Once cut and infolded, adaptation to the tension conditions of the abdominal wall is no longer possible. But, because of edematous swelling of inner organs during the course of peritonitis, the tension of the abdominal wall can increase considerably, with the danger that the sutures tear out. On the other hand, the edges of the incision must be brought together again gradually to the final suture of the abdominal wall later, during the healing phase in which the swelling of the inner organs decreases. Further, the typical complications of snap closures must be taken into account (constriction, tenaculum). There is no particular edge structure to infold into the fascia, so that only the individual sutures provide support. They are often not secure and tear out easily.

Continuous peritoneal lavage with a closed abdomen offers the advantage that an effective washing treatment can be started immediately after the operation, and thus, the purpose of the usual Redon suction drainage can be replaced considerably more effectively. The latter has a weak suction capacity, suctioning only right at the spot where it lays. Further, it easily becomes clogged and misleads to the assumption that the incision area has already been suctioned empty. With the sealed system, an intraperitoneal pressure can be built up and dosed. In doing so, the wash fluid (possibly with antibiotic added) also reaches the critical "atmospheric corners" of the abdomen. But not only are wash channels created, as when seepage through without pressure occurs. Fewer fibrin-induced adhesions are formed, since the abdomen contents "swim" and fibrin (among other things) is effectively washed out (thus, simultaneous ileus prophylaxis).

Peritoneal dialysis is possible. With it, an increase in the retention values (creatine, urea, potassium) with a threat of renal failure can conceivably be halted simply by using a commercially available dialysis fluid as the wash fluid. The patient can easily be dialyzed, without having to be put into the expensive program of hemodialysis. The associated drawbacks are also eliminated, as they can sometimes occur during the handling of blood volume. Washing can be taken over by a machine according to a desired program; thus, clear relief for the nursing personnel is possible. A chamber count of the leukocytes in the wash fluid makes it possible to monitor simply the response of the peritonitis. A judgment of the efflux can conceivably be performed simply by inspection (cloudiness, fibrin or blood admixtures). Wash fluid sensors to determine the resistance of bacteria can be removed by the catheter at any time, just as other substances can be administered (e.g., electrolytes, protein, heparin). The drawback here is that the abdomen is no longer accessible and thus no direct visual monitoring exists any more, which is important, when the efflux changes pathologically or the clinical condition of the patient worsens. Packing and infection source of the drainage passage points, as well as clogging or obstruction of the drainages represent typical complications. If the abdomen must be accessed again, a relaparotomy must be performed.

Despite promising starts, the strategy of the closed abdomen has not been able to be used in practice, since the drawbacks predominate.

SUMMARY OF THE INVENTION

The object of this invention is to improve a temporary intracorporeal surgical closure of the above-mentioned type so that a completely pressure-tight closure is obtained that still can be opened at any time, as often as desired. Further, the possibility of repeatable, continuous regulation of the tension of the abdominal wall is to exist and thus also intraperitoneal pressure, without having to break the critical connection between the edge of the securing element and the corresponding layer of body tissue.

This object is achieved by providing a securing element that surrounds the surgical incision on all sides and has an access opening above the surgical body opening. Furthermore, a tube surrounds the access opening and extends upwardly from it, this tube either serving as the closure or carrying it.

With this invention, the advantages of both above-mentioned strategies can be combined, so that new, broadened therapeutic possibilities are available, for example, in abdominal surgery, whose use does not remain limited to the treatment of peritonitis but also appears promising, for example, in the treatment of pancreatitis. A temporary closure of the abdominal cavity is used mainly when postoperative complications are to be expected. Use as a temporary closure of other body cavities is also possible.

With integrated connections for drainage hoses, the advantages of a continuous, closed washing system or peritoneal dialysis can simultaneously be exploited. By a particular design and by forming the edge structure, a further improvement can be achieved that makes it possible to connect the base plate and the fascia nonpositively and tightly. A fibrin gluten can also be used.

Other advantageous details of the invention are described below in more detail based on the embodiments illustrated in the drawing.

BRIEF DESCRIPTION OF THE DRAWINGS

FIG. 3a is a partial enlargement of detail E of FIG. 3, FIG. 3b and FIG. 3c show other possibilities for connecting the securing element to the fascia in the form of a clip closure.

DETAILED DESCRIPTION OF THE PREFERRED EMBODIMENTS

The surgical closure according to the invention can be sutured on, as a temporary closure of the abdominal cavity, into fascia 1, that is the aponeurosis of the abdominal wall, on the underside of abdominal wall 2.

Figure 3:
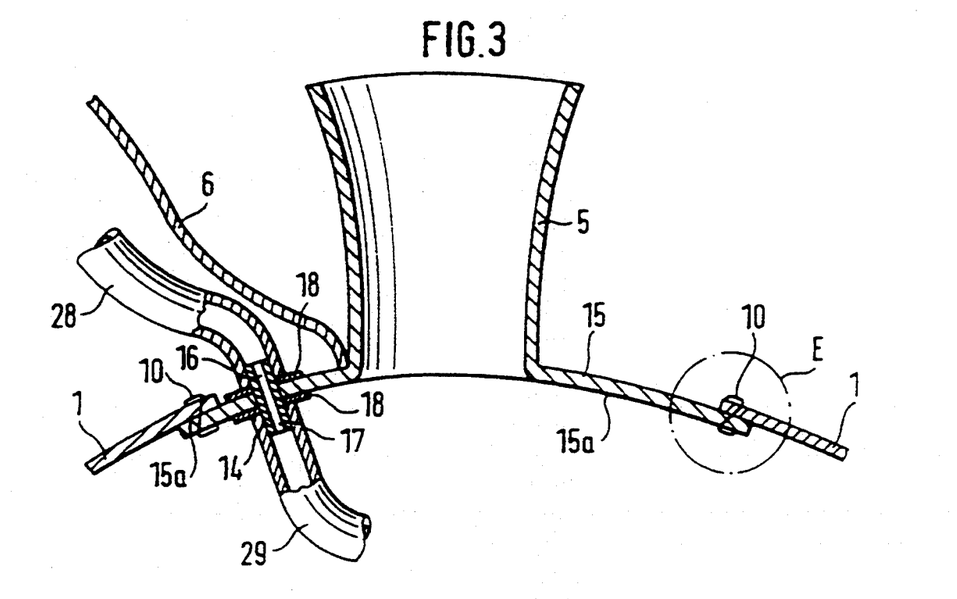
FIG. 3 is a cross section through the surgical closure according to FIG. 1, along cut line I—I in FIG. 2.
Figure 3A:
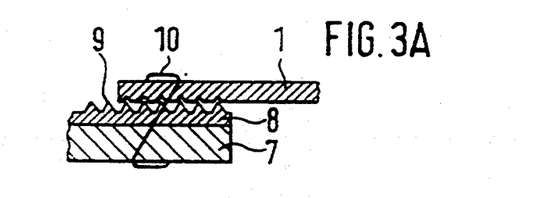

For this purpose, after selection of the appropriate size from among numerous types of surgical closures, with respect to the length of the abdominal incision, edge 3 of a single securing element 15 that surrounds the incision on all sides, and that is referred to hereafter as base 15a, with its opening 4 placed above the surgical incision is pushed under fascia 1 on all sides and, according to a possible embodiment according to FIGS. 3 and 3a, is sutured to fascia 1. Here, opening 4, selected according to the incision length, can be adapted to the periphery of the incision, whose opening depends on the tension of the abdominal wall. This is achieved, mainly, when opening 4 is designed as a section that reaches far into the corners in the form of a lancet or approximately an ellipse or a wide fissure with rounded face ends. A condition for this possible adaptation of opening 4 is further that base 15a consists of flexible material that, in addition, can be stretched elastically. But, the elasticity is not to be too great, to be able still to generate sufficient crosswise tension in the direction in which the incision is pulled together.

Figure 4:
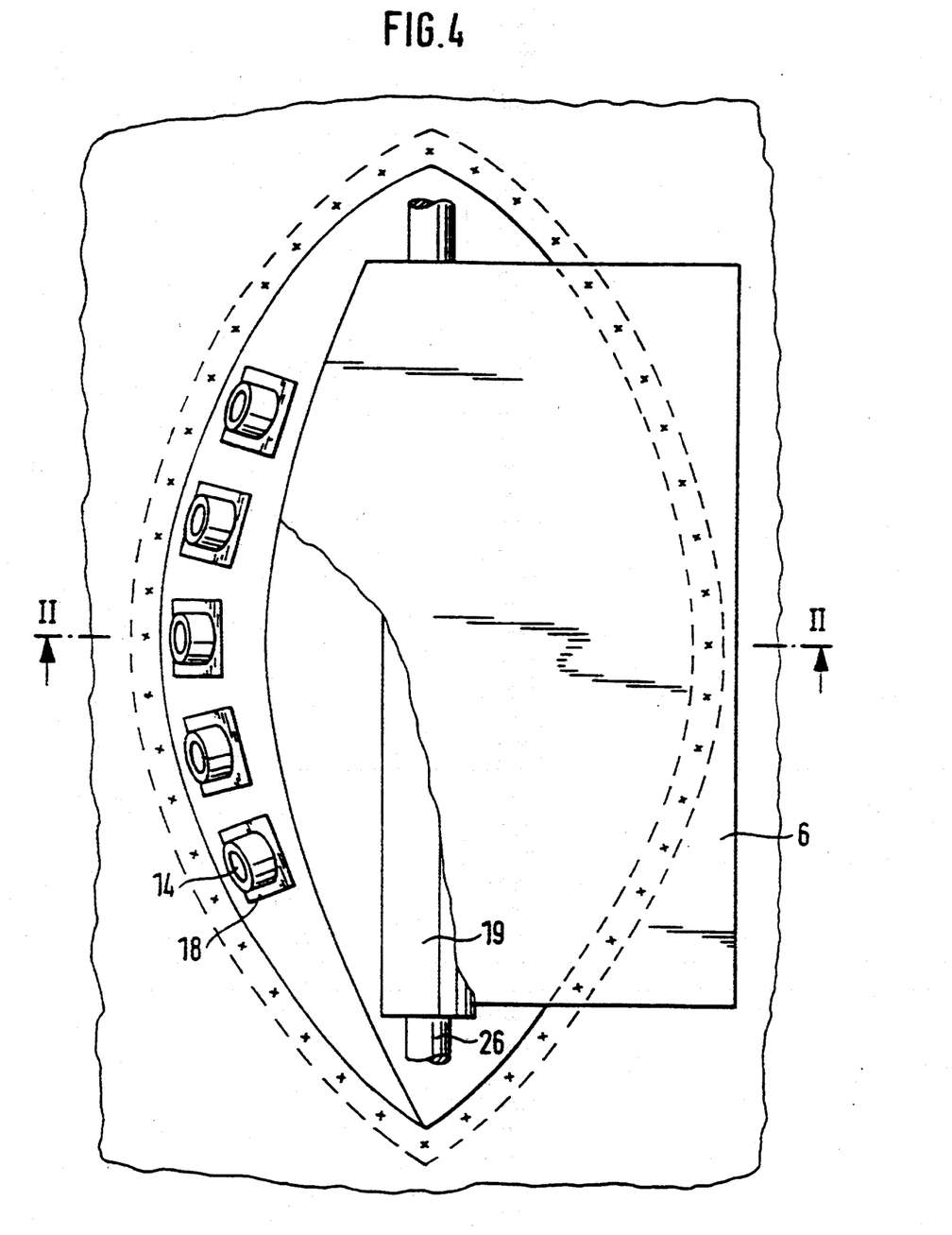
FIG. 4 is a top view of the surgical closure according to FIG. 1 in the closed state.

Opening 4 is surrounded, for example, by a hose or funnel-shaped tube 5 that is placed, at a distance, perpendicular to base 15a and consists of flexible material with optionally limited elasticity. The term tube is to be understood as a pipe-shaped object of any cross sectional shape that extends away from opening 4, i.e., away from the incision, and forms, over its entire length, a fluid-tight cuff. On one side of tube 5, outside it, on base 15a or on tube 5, a cover flap 6 is provided which, after folding tube 5, for example folding it together and/or rolling it together, is thrown over the folded or rolled tube 19 (FIGS. 4 and 5), and can be attached on the other side of tube 5 to base 15a, so that the length by which it is thrown over can be changed.

But, another embodiment is conceivable in which the material for base 15a, for tube 5 and also for cover flap 6 is selected with respect to elasticity so that a suddenly occurring increase in intra-abdominal pressure, such as a cough, can be at least partially compensated for. In this way, the forces acting on the connection between base 15a and fascia 1 are reduced in any case.

To make it possible to have a connection between base 15a and fascia 1 that grips frictionally and is tolerated by the tissue, edge 3 of the securing element must fit or grip sufficiently far underneath fascia 1 on all sides, must consist of biocompatible or tissue-compatible material and must have a suitable structure. As a biocompatible material, a textile fabric known by the trademark "Goretex," as it is already used in vascular surgery, is especially suitable. Such blood vessel prostheses can be infolded tightly and withstand blood pressure peaks up to 200 mmHg systolic.

Figure 1:
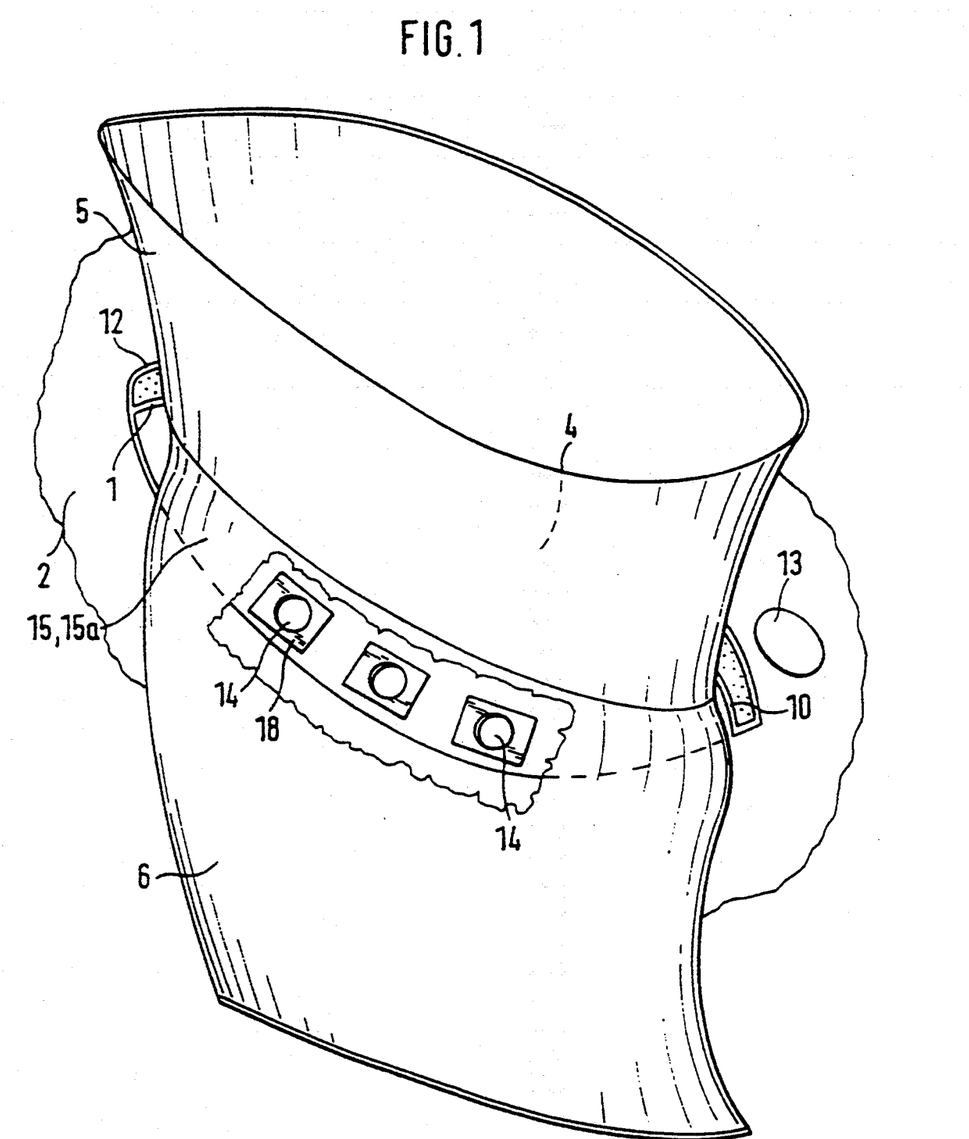
FIG. 1 is a view of a surgical closure according to the invention.
Figure 2:
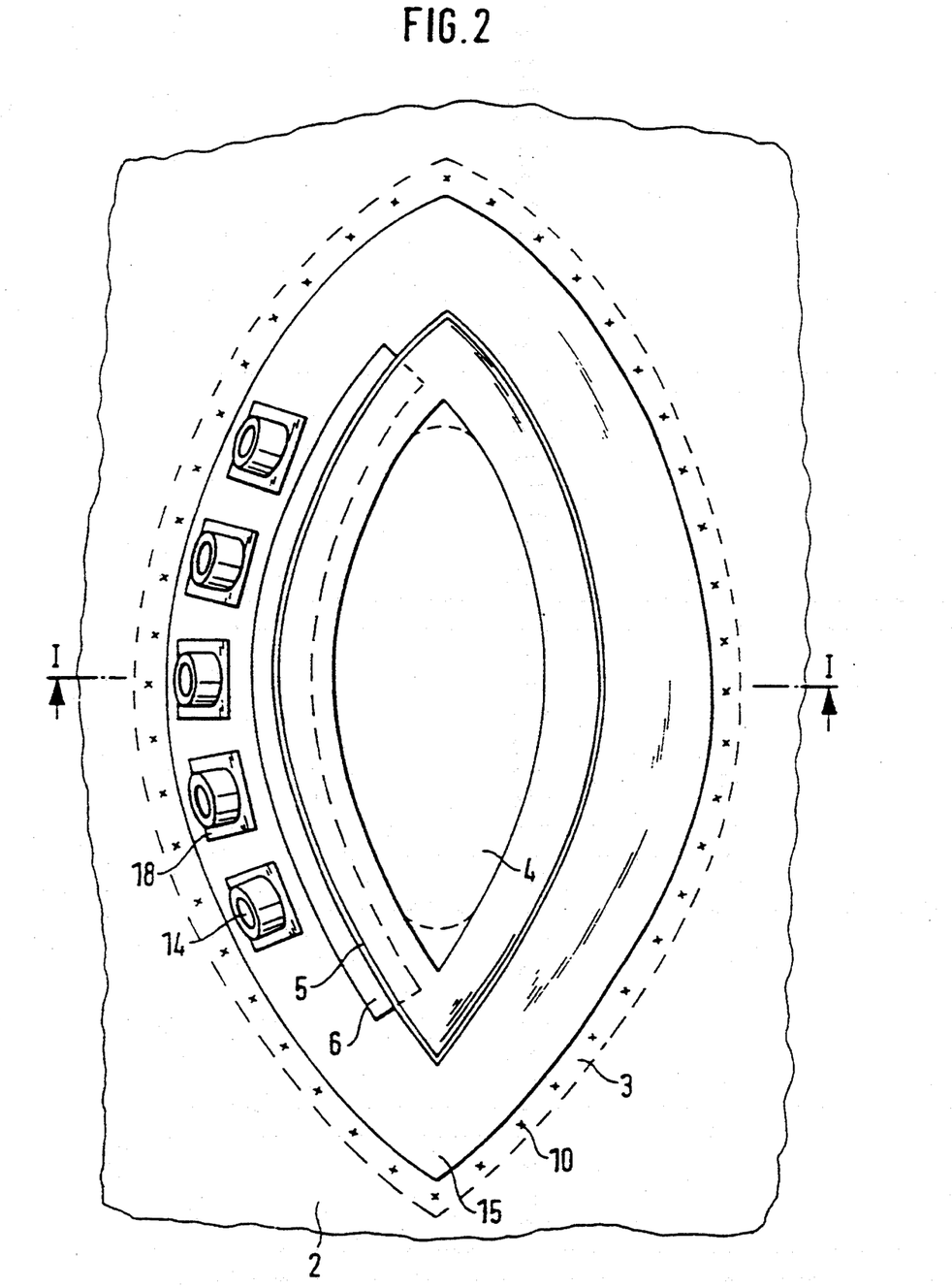
FIG. 2 is a top view of the surgical closure according to FIG. 1 in the open state.

In the framework of this invention, there are several possibilities for the design of edge 3. If a simple embodiment does not meet the requirements of a stable and tight connection between base 15a and fascia 1, not even with the support of an adhesive, preferably a fibrin gluten, then edge 3 can be made as represented in FIG. 3a. A sufficiently stiff lower layer 7 distributes the pressure, which is generated by the suture or by several sutures 10, over a large area against fascia 1 and simultaneously provides a bracing layer for the fine tips or teeth 9 that grip two-dimensionally into fascia 1. Tips or teeth 9 project from a soft sealing layer 8 that is placed above lower layer 7. Suture 10 grips, in the simplest case, only fascia 1, but can also grip, depending on the suture technique, such as with a burst abdomen, all layers of abdominal wall 2 and be braced by a pressure-distributing disk 13 (FIG. 1) on skin 12. Further, it is conceivable that, to produce a tight suture on fascia 1, a suture or clamp device would be used. The connection can also additionally be supported by a fibrin gluten and sealed. In this connection, the use of silicone as an additional sealing material is conceivable.

In making suture 10 between fascia 1 and base 15a, it is especially advantageous that there be unhindered access through central opening 4 to the surgical incision, since opened tube 5, because of its flexibility, can be collapsed flat or folded flat. The needle path on the intraperitoneal side can be monitored visually. Optionally, abdominal cavity content(s), e.g., sections of intestine, can be pushed out of the way of the intraperitoneal needle path. Next to edge 3, preferably on one side of securing element 15, several drainage connections 14 are integrated into base 15a or can be attached there afterward and are equipped with a screw thread for upper connecting part(s) 16 that lead(s) outward and for lower connecting part(s) 17 that lead(s) inward. If no drainages are in use, upper connecting parts 16 are closed with screw stoppers. The drainage passages are incorporated, in a preferred embodiment, in two reinforcement plates 18 that surround base 15a from above and below two-dimensionally and in a pressure-tight way. If one or more drainages is used, they can be placed, when tube 5 is opened, in the abdominal cavity and be screwed onto lower connecting part 17. Extracorporeal drainage 28 can be screwed, as a continuation, even when tube 5 is closed, onto upper connecting part 16. Since in doing so the problems of sealing and a source of infection at a loose drainage passage point are eliminated, as they appear in part when separate catheters are guided through the abdominal wall, it is simpler to decide to use several drainages by integrated drainage connections 14 and to design the system basically also for drainages with wider lumina. Because of the simple intra-abdominal accessibility, the possibility exists, even when intracorporeal drainage 29 stops functioning, to eliminate the intra-abdominal cause through opening 4.

Tube 5, open upward, rises from where it is attached on the inside edge of base 15a. Tube 5 is connected to base 15a integrally and in a pressure-tight way and can close central opening 4, and thus the abdominal cavity, in a pressure-tight way.

According to a preferred embodiment, tube 5 is closed by a rolling-up operation by a two-piece rod 26, for example.

Figure 5:
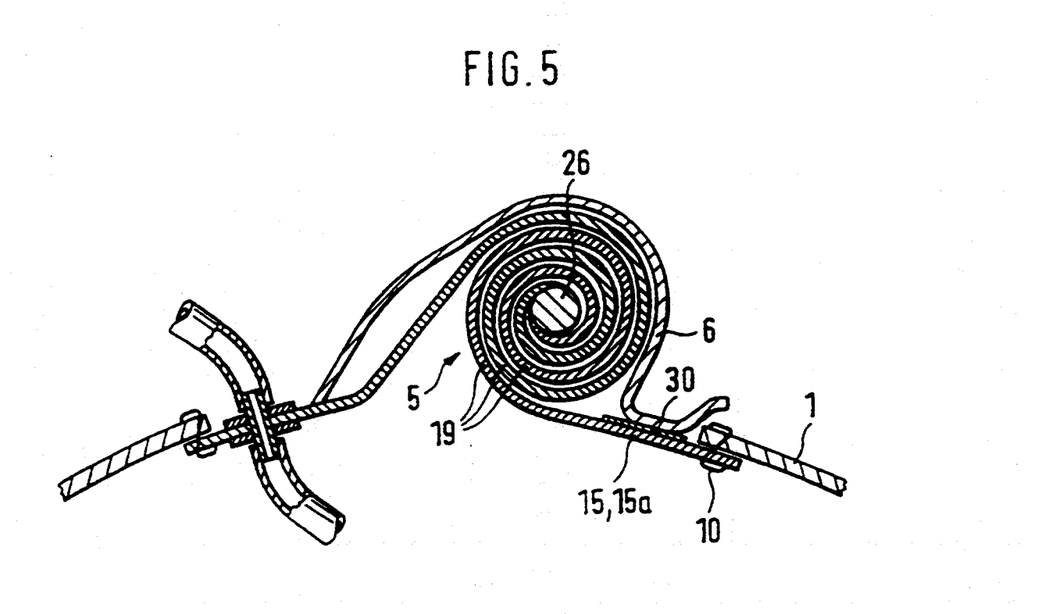
FIG. 5 is a cross section through the surgical closure according to FIG. 1, along cut line II—II in FIG. 4, and, FIG. 5a is a partial enlargement of FIG. 5.
Figure 5A:
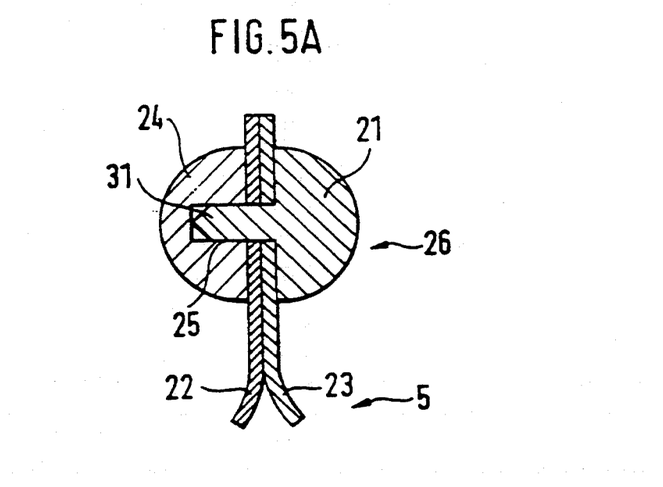

FIG. 5a shows that rod half 21 has pointed pins 31 on it that pierce both upper, collapsed walls 22, 23 of tube 5 and collapsed tube walls 22, 23 can be folded in advance. Second rod half 24 is pressed by corresponding recesses or holes 25 onto pins 31 of first rod half 21. Secured in this way, folded tube 5 can be rolled up by rod 26, made as a round rod, and formed into rolled tube 19. Depending on how far it is rolled up and how the lengthwise profile of rod 26 is configured, (e.g. the rod can have a diameter which varies along its length) various partial tensions can be generated on the edges of the incision. Rolled-up tube 19 is now finally secured with cover flap 6. This cover flap 6 is integrally connected to base 15a on the side of drainage connections 14. Coverflap 6 is extended over rolled-up tube 19 and is attached on the other side. Preferably, an adhesive closure, such as a hook and pile closure 30 of the type sold under the trademark VELCRO, is used.

In another embodiment, rod 26 can be used exclusively as an aid to rolling and be removed after the rolling-up operation. The ends of rolled tube 19 can also be folded inward and thus be secured by cover flap 6 that grips above it. In special cases, it can make sense to use a type of abdominal belt as an additional securing means.

Figure 3B:
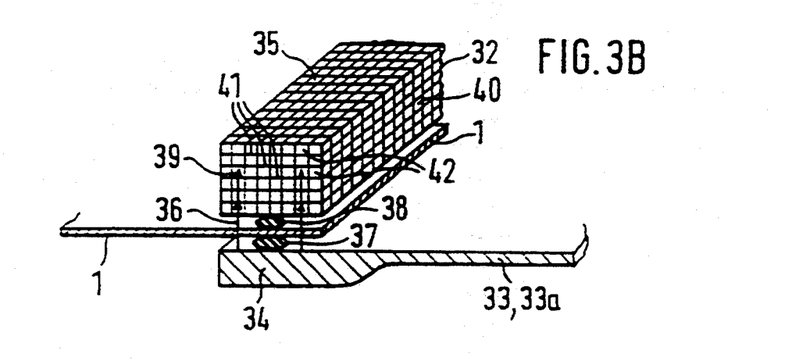

According to another embodiment, as represented in FIG. 3b, the tight closure between fascia 1 and base 33a of securing element 33 can be made as a clamping closure 32 as follows.

To make it possible to achieve a frictional, optionally combined frictional and interlocking, as well as tight, connection that grips surface wise between base 33a of securing element 33 and fascia 1, inner edge 34 of securing element 33 must grip or fit sufficiently far under all sides of fascia 1, so that clamping fastener 35 pressed from above onto inner edge 34 can pinch fascia 1 sufficiently strongly and tightly.

As FIG. 3b shows, inner edge 34 of clamping closure 32 preferably has a width of about 2 cm and it is equipped with barbs 36 that are preferably one to two cm long. Pressed against a clamping fastener 35 emplaced from above, these barbs 36 pierce, from below, fascia 1 and possibly also part of the muscle layer connecting from above. Into clamping fastener 35, which preferably are made as lattice block 40, barbs 36 can engage to varying extents, depending on pressure, in the individual openings of lattice block 40, in the corresponding horizontal layers or lattice planes 41 of lattice block 40. Additional inner and outer seals 37, 38 seal clip closure 32 fluid-tight. It is possible in a simple way to press together both complementary clamping fastener parts 35, 36 simultaneously with the thumb and forefinger of one hand since, by central opening 4, the forefinger can grip around folded tube 5 under base 33a. Individual fasteners 35, cut with a suitable cutting tool in an appropriate shape and length, seal all around the edge of the incision.

With the use of lattice blocks 40 as clips 35, the former consist of one or more lattice planes 41 which, to produce a solid locking connection, are provided with openings 42 that correspond to teeth 39 of barbs 36.

To assure a secure sealing of the clip closure according to FIG. 3b, sealing elements 37, 38 that completely surround incision opening 4 are provided in edge area 34 where securing elements 33 grip underneath, between securing element 33 and fascia 1 on the one hand and, on the other hand, between fascia 1 and fasteners 35.

It is important that, when using several lattice blocks 40, they be distanced from one another along incision opening 4 so that they can be moved laterally with respect to one another along incision opening 4.

According to another variant embodiment, fasteners 35 can consist of elastically flexible solid material, for example of a rubbery material or of rubbery plastics, into which barbs 36 can be pressed to produce a sufficiently connection.

The detachment of lattice blocks 40 or generally of fasteners 35 from the inner edge of base 33a of securing element 33 is suitably performed by a lever tool known in the art.

Figure 3C:
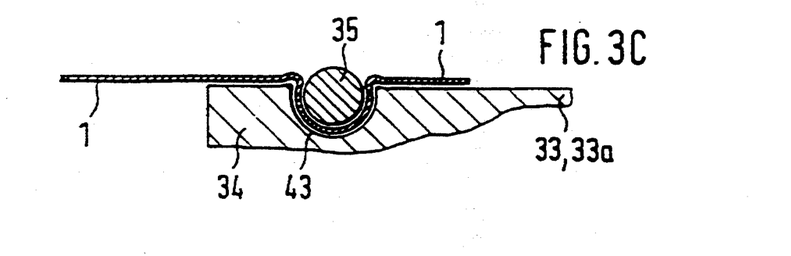

According to the embodiment according to FIG. 3c, inner edge 34 of base 33a of securing element 33 has a recess 43 that completely surrounds incision opening 4, a recess that tapers in cross section on the surface toward fascia 1, so that one or more fasteners 35 can be engaged as a sealing element in this recess 43 with the interposition of fascia 1, optionally in connection with other body tissue structures. Preferably, fasteners 35 have a circular cross section, so that they can be snapped into likewise approximately circular recess 43 and, because of the elastic design of securing element 33, are secured in a nonpositive, interlocking way, in this position. This a traumatic clip closure is distinguished in that a preferably slightly flexible, cuttable rod, preferably a round rod, can be pressed into mentioned recess 43 and in that it is assured, with this clip connection, that interposed fascia 1 is not injured.

As a supplement to the previous embodiment, it can also be suitable to put markings, for example in the form of numbers, letters, symbols or the like, on base 15a or 33a of securing element 15 or 33.

It is also advantageous if the entire surgical closure, or at least those parts of it that directly touch, or can touch, body tissue, consist of a biocompatible material such as, for example, the above-mentioned, known textile material known by the commercial name "Goretex."

Even when, as can be seen especially from FIGS. 3 and 5, tube 5 and securing element 15 are preferably made as one piece, it lies within the framework of a possible modification of the invention to configure tube 5 and securing element 15 as separate components and to connect them tightly to one another subsequently.

According to a preferred embodiment, securing element 15 consists of a single component. But, this does not exclude the possibility of producing securing element 15 from several securing element parts and connecting them tightly to one another.

Suitable as materials for tube 5 are flexible plastic foils or textile synthetics whose surface can be provided with plastics or with other sealing and/or tissue-compatible materials.

Other advantages of the surgical closure according to the invention are to be seen in the use of laparoscopy. For this purpose, adapter parts, for example, can be attached to drainage connections 14, through which laparoscopical examinations and/or procedures can be performed.

Finally, it is also advantageous that the surgical closure according to the invention makes it possible to have various washing or washing-suctioning patterns. Even postoperative, continuous, open dorsoventral abdominal washing can be easily done with the temporary abdominal wall closure according to the invention. The complicated, disadvantageous palisade stabilization of the surgical opening is eliminated here. Drainage connections 14 can be used as a wash inlet, and a widelumen drainage, placed in tube opening 4 and sealed to tube 5, for example, with a tube clamp or a first-aid bandage, can be used as a suction pipe. Further, a probe for measurement and continuous monitoring of the intraperitoneal pressure can be connected by a drainage connection 14 as a permanent access.

Finally, with the clip closure according to the invention, a quicker implantation is possible than with timeconsuming infolding.

We claim:

1. Surgical closure comprising a securing element having single edge member for extending around a surgical incision on all sides, said edge member being tightly, detachably securable within body tissue adjacent the incision and being provided with an access opening for providing access to substantially the entirety thereof, and a closure for enabling repeated opening and closing of said access opening, said closure comprising a tube attached to said edge member and through which access to said access opening and the incision is obtainable, said tube surrounding the access opening and extending upwardly therefrom; and wherein said edge member and said tube are formed of a flexible material which forms a means for enabling the size of said access opening to be physically varied to conform to the width of the surgical incision.

2. Surgical closure according to claim 1, wherein the access opening is lancet- or elliptically-shaped.

3. Surgical closure according to claim 1, wherein the tube is secured to on the edge member in a pressuretight manner.

4. Surgical closure according to claim 1, wherein at least those portions which contact body tissue are formed of a biocompatible material.

5. Surgical closure according to claim 1, further comprising a cover flap; wherein said tube is collapsible; wherein said cover flap is mounted to said edge member on a first side of said tube and is of a size and shape to extend over and cover said tube when it is in a collapsed state; and wherein said cover flap is detachably securable to said edge member at a second, opposite side of said tube.

6. Surgical closure according to claim 5, wherein an adhesive closure is provided for detachable securement of said cover flap, selectively, at various points along the length of the cover flap.

7. Surgical closure according to claim 5, wherein said tube is foldably collapsable.

8. Surgical closure according to claim 5, wherein said tube is rollably collapsable.

9. Surgical closure according to claim 8, wherein a rod is provided having a length which is greater than a width of said tube, said forming a means for rollably collapsing said tube starting at a free end thereof.

10. Surgical closure according to claim 9, wherein said rod is attachable to said tube at said free end thereof.

11. Surgical closure according to claim 9, wherein said rod has a diameter that varies along its length.

12. Surgical closure according to claim 1, wherein said tube is rollably collapsible; and wherein said closure further comprises securing means for holding said tube in a rolled state.

13. Surgical closure according to claim 12, wherein said securing means comprises an adhesive closure.

14. Surgical closure according to claim 1, wherein said edge member has at least one marking symbol thereon.

15. Surgical closure according to claim 1, wherein at least one drainage hose connection is attached to said edge member in proximity to said tube.

16. Surgical closure according to claim 15, wherein said edge member is provided with a plurality of drainage hose connections.

17. Surgical closure according to claim 15, wherein said at least one drainage hose connection is secured to said edge member.

18. Surgical closure according to claim 1, wherein a rod is provided having a length which is greater than a width of said tube, said rod forming a means for rolling-up of said tube, said rod being divided lengthwise into rod halves, one of said rod halves having projecting pins and the other having holes, the projecting pins being retainable in the holes after having pierced portions of said tube.

19. Surgical closure according to claim 1, wherein stud securing element has a clamping closure for securement of the edge member to fascia of the body tissue.

20. Surgical closure according to claim 19, wherein the clamping closure is provided at an edge area of the securing element and comprises a base member with barbs for engaging underneath the fascia and a clamping fastener for interlocking with said barbs after they have pierced said fascia.

21. Surgical closure according to claim 20 wherein said clamping fastener comprises at least one lattice block.

22. Surgical closure according to claim 21, wherein said at least one lattice block is formed of a plurality of planes with openings, said barbs having teeth for interlocking in the openings of said planes.

23. Surgical closure according to claim 21, wherein said clamping fastener comprises a plurality of lattice blocks spaced relative to each other.

24. Surgical closure according to claim 20, wherein sealing elements are provided surrounding the access opening on the an edge area of the base member and on said clamping fastener for engaging the facia at each of opposite sides thereof.

25. Surgical closure according to claim 20, wherein said clamping fastener comprise an elastically flexible solid material into which said barbs can be pressed.

26. Surgical closure according to claim 19, wherein the clamping closure is provided at an edge area of the securing element and comprises a base member having a recess completely surrounding the access opening and a clamping fastener which is engageable in said recess with at least the facia of the body tissue interposed therebetween.

27. Surgical closure according to claim 26, wherein the recess has a circular cross section and said clamping fastener is a rod.

* * * * *